United States Patent
Daniels et al.

(10) Patent No.: US 9,596,902 B2
(45) Date of Patent: Mar. 21, 2017

(54) EARMUFF ACCOMMODATING WELDING SHIELD

(71) Applicant: 3M INNOVATIVE PROPERTIES COMPANY, St. Paul, MN (US)

(72) Inventors: Bjorn Daniels, Vikarbyn (SE); Mats U. Sernfalt, Leksand (SE); Oskar E. Juhlin, Gustavsberg (SE)

(73) Assignee: 3M Innovative Properties Company, St. Paul, MN (US)

( * ) Notice: Subject to any disclaimer, the term of this patent is extended or adjusted under 35 U.S.C. 154(b) by 312 days.

(21) Appl. No.: 14/291,506

(22) Filed: May 30, 2014

(65) Prior Publication Data
US 2015/0342282 A1 Dec. 3, 2015

(51) Int. Cl.
*A42B 3/16* (2006.01)
*A61F 11/14* (2006.01)
*A42B 3/14* (2006.01)
*A61F 9/06* (2006.01)
*A42B 3/22* (2006.01)

(52) U.S. Cl.
CPC ............. *A42B 3/16* (2013.01); *A42B 3/145* (2013.01); *A42B 3/225* (2013.01); *A61F 9/06* (2013.01); *A61F 11/14* (2013.01)

(58) Field of Classification Search
CPC .................................. A61F 9/06; A61F 9/065
USPC .......................................................... 2/8.2, 9
See application file for complete search history.

(56) References Cited

U.S. PATENT DOCUMENTS

| | | | | |
|---|---|---|---|---|
| 1,820,237 A | * | 8/1931 | Malcom | A61F 9/02 2/8.2 |
| 1,885,426 A | * | 11/1932 | Flood | A61F 9/06 2/8.2 |
| 2,606,321 A | | 8/1952 | Malcom, Jr. | |
| 3,079,609 A | * | 3/1963 | Hoffmaster | A42B 3/14 2/8.1 |
| D509,323 S | | 9/2005 | Emilsson | |
| 7,188,622 B2 | | 3/2007 | Martin | |
| D663,900 S | | 7/2012 | Karlsson | |
| D663,902 S | | 7/2012 | Karlsson | |
| 8,243,943 B2 | | 8/2012 | Nordin | |
| D668,392 S | | 10/2012 | Carlborg | |
| D671,273 S | | 11/2012 | Carlborg | |
| 8,701,212 B2 | | 4/2014 | Daniels | |
| 2007/0245466 A1 | | 10/2007 | Lilenthal | |
| 2011/0113537 A1 | | 5/2011 | Peng | |

FOREIGN PATENT DOCUMENTS

| | | |
|---|---|---|
| CN | 202135768 | 2/2012 |
| KR | 2009-0095145 | 9/2009 |
| TW | M369144 | 11/2009 |

OTHER PUBLICATIONS

U.S. Appl. No. 29/492,350 to Daniels filed May 30, 2014, entitled Helmet Bracket.

(Continued)

*Primary Examiner* — Gloria Hale

(57) ABSTRACT

A welding helmet 10 that has a face shield 12 that has a native width NW and that has a lens 14 disposed in the face shield 12. A spreader bar 30 can expand the face shield 12 from its native width NW to an increased width IW to allow the welding shield 10 to easily accommodate earmuffs 16 worn by the welder.

18 Claims, 4 Drawing Sheets

(56) References Cited

OTHER PUBLICATIONS

U.S. Appl. No. 29/492,353 to Daniels filed May 30, 2014, entitled Helmet Bracket Having Arrow Indicia.
U.S. Appl. No. 29/492,357 to Daniels filed May 30, 2014, entitled Helmet Bracket Connector End.
International Application PCT/US2015/029669 Search Report dated Jul. 29, 2015.

* cited by examiner

EARMUFF ACCOMMODATING WELDING SHIELD

The present invention pertains to a welding shield that can expand widthwise to enable earmuffs to be comfortably worn under the shield.

BACKGROUND

Welding shields are commonly worn by welders to protect their eyes from bright light displayed by a welding torch and to protect their face from molten metal and sparks created during the welding process. Oftentimes welders also need hearing protection, since welding operations frequently occur in noisy environments. Earmuffs are a desired form of hearing protection for many welders because they can be applied without prior hand washing. Earmuffs, however, are fairly large in size, and accordingly can interfere with the placement of the welding shield on the welder's head. Welders, therefore, often need to step out of the work environment to wash their hands before inserting earplugs or to go without hearing protection. Although special welding shields have been manufactured to accommodate concomitant earmuff use, these shields tend to be bulky in size, making them difficult to use in narrow spaces. Specially adapted shields also tend to let indirect light in from behind the shield, which light interferes with the welder's vision. Further, the wider-sized shield can allow sparks to enter the shield from behind when the earmuffs are not being worn. The welder therefore may own two shields: one for welding usage with earmuffs and another for welding usage without earmuffs.

SUMMARY OF THE INVENTION

The present invention pertains to a new welding shield that comprises a face shield that has a first manufactured width, a lens disposed in the face shield, and a spreader bar that can expand the face shield from its native width to an increased width.

The present invention also pertains to a spreader bar that is useful for expanding the width of a welding shield. The spreader bar comprises an arcuate portion and first and second shield attachment ends. The arcuate portion is located between the first and second attachment ends. Together the arcuate portion and the attachment ends provide the spreader bar with a resistance to compression of at least about 30 Newtons when tested according to the Resistance to Compression Test.

The present invention provides a new welding shield and a spreader bar that overcome the above-noted drawbacks. In particular, the inventive welding shield and spreader bar allow the welder to use the same welding shield when wearing earmuffs and when not wearing earmuffs. The spreader bar expands the welding shield from its native width to a wider width to enable the shield to accommodate earmuff usage. Welders also no longer need to resort to hand washing and earplug use in achieving hearing protection when using their regular welding shield.

GLOSSARY

The terms set forth below will have the meanings as defined:

"face shield" means a solid structure disposed at least in front of a person's face when the welding shield is worn and that can support a lens;

"increased width" means a distance measured between first and second sides of the face shield at the temporal location, which distance has been measured after the native width has been altered by implementation of an external force;

"lens" means a solid structure through which a person can see objects when looking therethrough (from the inside outwardly);

"native width" means a distance measured between first and second sides of the face shield at the temporal location when the shield is in its intended shape without any force(s) being exerted thereon;

"spreader bar" means a device that is attachable to a welding shield and that is capable of exerting a force thereon to expand the welding shield width beyond its native width;

"temporal location" means a measurement taken between two opposing points located on a plane that transversely bisects the face shield lens at the rearward perimeter of the face shield; and "welding shield" means a device that is worn by a person on their head to protect the person during welding operations.

DETAILED DESCRIPTION OF PREFERRED EMBODIMENTS

The present invention provides a welding shield that has a face shield that has a first manufactured or native width, which can expand to a second increased width. The width expansion is provided by a spreader bar that can be attached to the face shield interior. The spreader bar causes the face shield to increase in width so that the welder can wear earmuffs beneath the face shield when in a noisy environment. Hearing protection is often needed when welding, and earmuffs are a common form of hearing protection for welders because the muffs do not generally necessitate washing of hands before placement on the head. Most earplugs require the user to twirl and compress the plug between the fingers before insertion into the ear. Earplug users accordingly must wash their hands first. Because the earmuffs project a few centimeters from the wearer's head, the muffs can interfere with welding shield placement on the head. The present invention is beneficial in that welders no longer need to go to a sink to wash their hands before inserting earplugs. Nor do they need to have a second larger shield that does not interfere with earmuff use The present invention accordingly allows one shield to be used for welding with or without earmuffs.

In describing the inventive welding shield and spreader bar, the words "a", "an," and "the" may be used interchangeably with "at least one" to mean one or more of the elements being described. For facilitating the following description, and when viewing a welding shield of the invention, as projected onto a plane, a transverse or horizontal dimension extends across an upright shield, and a longitudinal dimension extends between the bottom and the top of the shield in a vertical direction.

Figure 1:
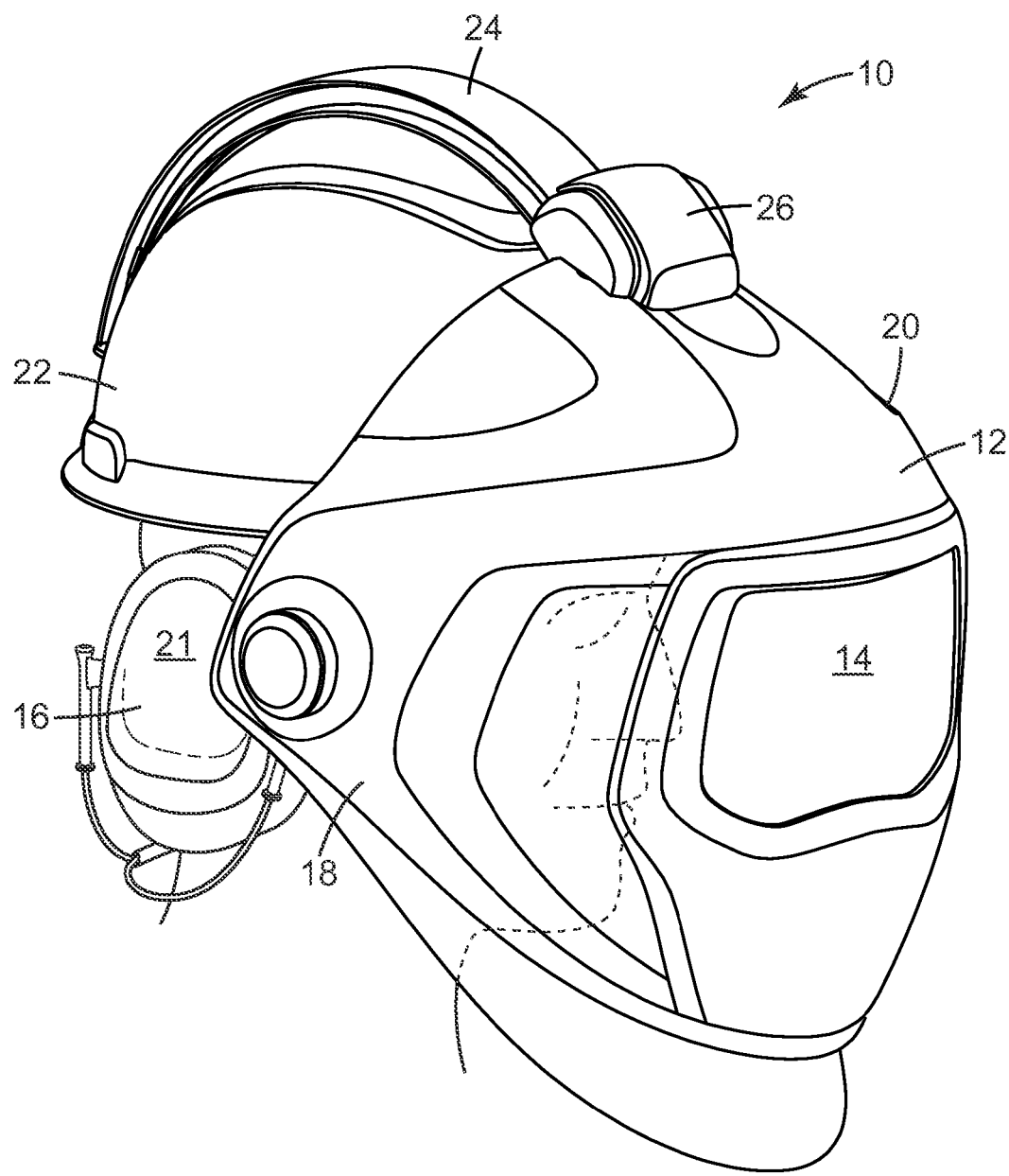
FIG. 1 is a perspective view of a welding shield 10 in accordance with the present invention.

FIG. 1 shows a welding shield 10 that has a face shield 12 into which a lens 14 is disposed. The face shield 12 is shown in an expanded condition, which allows the face shield 12 to be worn over earmuffs 16. The face shield 12 has first and second sides 18 and 20 that become spaced further apart to accommodate the earmuffs 16 being worn by the welder. The distance between sides 18 and 20 preferably is increased to such an extent that the sides 18 and 20 do not make contact with the outer shell 21 of the earmuff 16. The earmuffs 16 are placed over each ear to attenuate sound in the ambient environment. The face shield 12 engages and is supported by a helmet 22 through attachment to an elongated guide 24 located centrally on the helmet along the sagittal plane. A face shield bracket 26 may be used to attach the shield 12 to the elongated guide 24. A description of a face shield that is removably attached to an elongated guide can be found in co-pending U.S. patent application Ser. No. 13/627,571 to Daniels et al. entitled Elongated Guide, and Visor Removably Mounted Thereto and in Ser. No. 14/177,299 to Daniels et al. entitled Appliance Mounting Device and System for Head Gear. Examples of earmuffs that may be used in connection with a welding shield of the present invention are described in U.S. Patents D668,392 and D671,273 to Carlborg et al., D663,900 and D663,902 to Karlsson et al., D509,323 to Emilsson, and U.S. Pat. No. 8,243,943 to Nordin et al. Commercially available products include, for example, passive earmuffs as 3M™ brand Peltor™ X-series or Optime™ I, II or III. Other examples include active headsets such as 3M™ Peltor™ Tactial, Twin Cup or Litecom Pro™.

Figure 2:
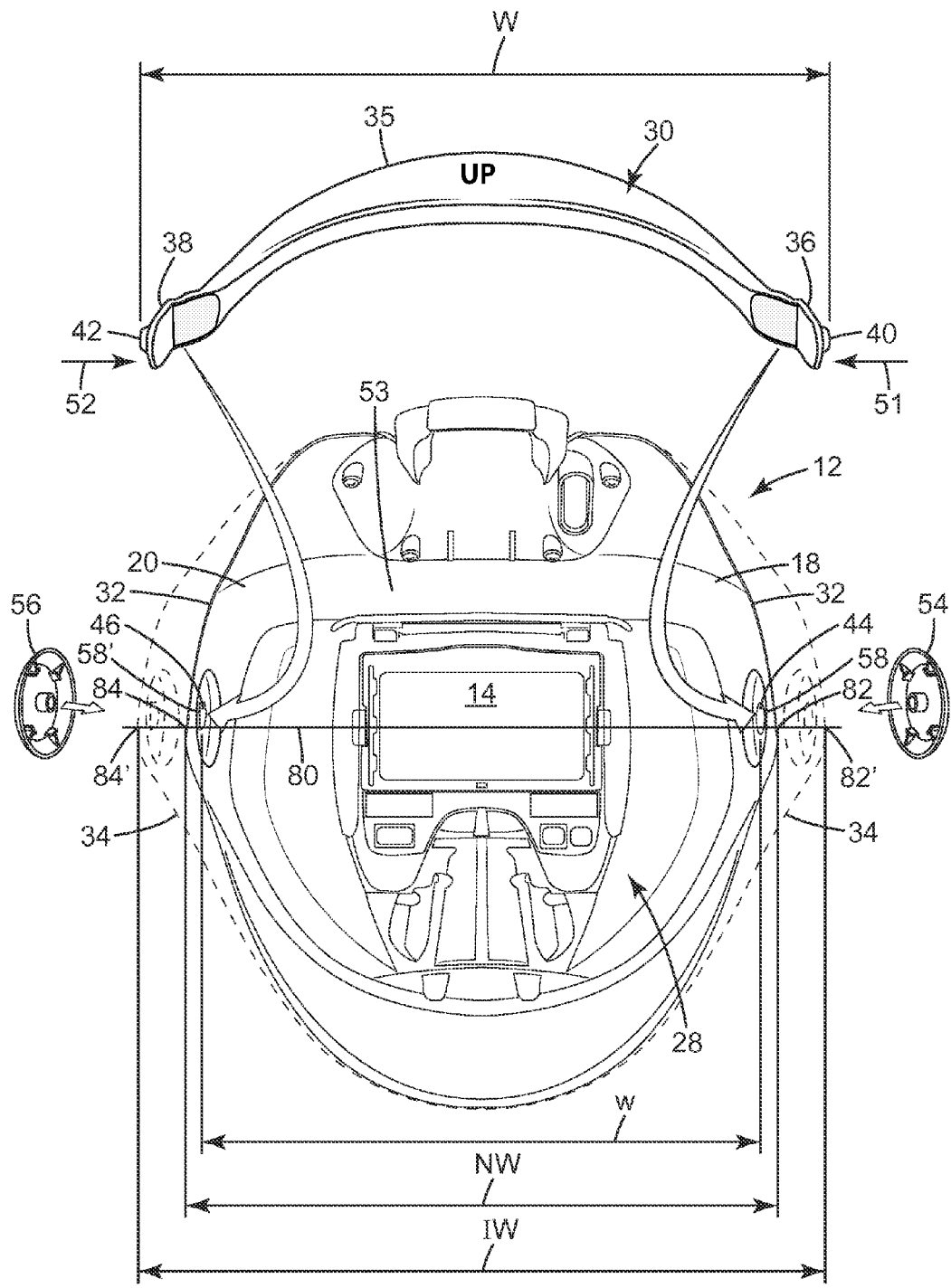
FIG. 2 is a rear view of a welding shield 10 in accordance with the present invention, showing the spreader bar 30 separated therefrom.

FIG. 2 shows the interior 28 of the face shield 12, in conjunction with a spreader bar 30. The spreader bar 30 is used to expand the face shield 12 of the welding shield 10 from its unexpanded condition 32 to its expanded condition 34. The spreader bar 30 includes a central arcuate portion 34 located between first and second shield attachment ends 36 and 38. Attachment end 36 attaches to the first side 18 of the face shield 12, and attachment end 38 attaches to second side 20. Each attachment end 36, 38 includes a means 40, 42 for securing the attachment end to the face shield 12. The width W of the spreader bar 30, prior to its securement to the face shield 12, is greater than the width w of the face shield 12 between attachment locations 44, 46. Width W typically is about 20 to 40 cm, more typically about 25 to 30 cm, and width w is typically about 15 to 30 cm. Width W typically is at least about 10 to 30 percent greater than width w. When the spreader bar 30 is attached to the face shield at locations 44, 46, the face shield 12 increases in width w from the unexpanded condition 32 to the expanded condition 34. The spreader bar 30 has a resistance to compression in the direction of arrows 51, 52, which is greater than the resistance to compression of the face shield at attachment locations 44, 46 in the same directions 51, 52. The greater width W over w and the greater resistance to compression of spreader bar 30 compared to face shield 12 cause the sides 18, 20 of the face shield 12 to move apart when the spreader bar is attached to the face shield. The movement outwardly—that is, the movement of sides 18 and 20 away from each other—is great enough to allow earmuffs to reside between the sides 18 and 20 of the face shield without interfering with the outer shell 21 of the earmuffs 16. The expansion of the face shield 12 from its first condition 32 to its second expanded condition 34 typically is greater than 1 centimeter (cm), more typically about 2 to 10 cm, still more typically about 2.5 to 5 cm. When the spreader bar 30 is secured to the face shield 12, the arcuate or bowed portion 35 of the spreader bar becomes located above the lens 14 in region 53. Protective and/or cosmetic caps 54, 56 may be secured to the face shield 12 to cover the exterior of the locations where the spreader bar securement means 40, 42 are joined to the face shield 12 at locations 44, 46. To secure the spreader bar 30 to the face shield 12, remove the two caps 54, 56 from the face shield 12 and orient the face shield 12 so that it can be viewed from the rear as seen in FIG. 2. The bowed portion 35 should point into the shield 12 with the two ends 36, 38 pointing to the rear. The spreader bar can be labeled "up" on the top surface 37 to assist with identifying the proper orientation of the spreader bar 30 relative to the face shield 12. Place the first end 36 into the first hole 58 at location 44 from the inside of the shield. Spread the face shield 12 while pushing the spreader bar 30 into position in shield 12. Typically, the shield 12 is spread wider than the uncompressed width W of the spreader bar 30 so that the securement means 42 can be placed in the second hole 58' at second location 46 in the shield 12. The caps 54, 56 may then be secured to the outer surface of the shield at locations 44 and 46.

Figure 3A:
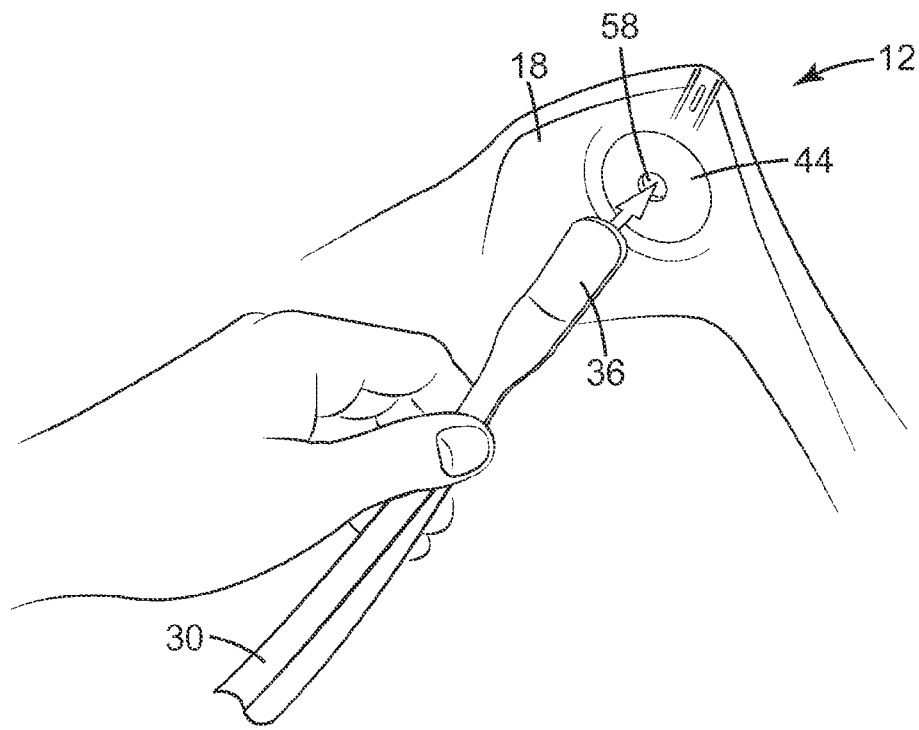
FIGS. 3a and 3b show the manual securement of the spreader bar 30 into an opening 58 on the face shield 12 at location 44.
Figure 3B:
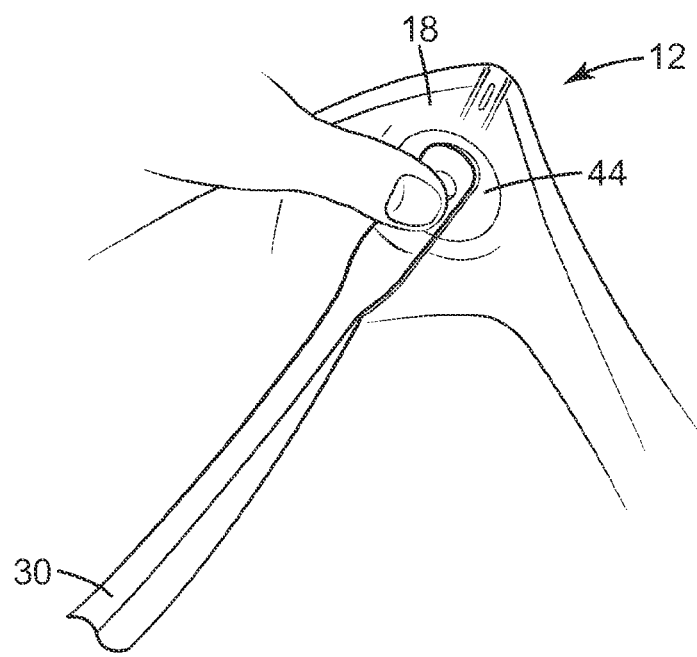

FIGS. 3a and 3b show one example of how the spreader bar 30 can be attached to the face shield 12. In this instance, the spreader bar 30 is manually snapped into place. The securement at the first side 18 of the shield 12 is accomplished simply by pressing the end 36 of bar 30 into the opening 58 at attachment location 44. The securing means 40 may be fashioned such that an audible "click" is heard when the proper engagement has been achieved. The securing means 40 may include a male member that is adapted to cause the snap fit into opening 58. The securing means 40, 42 provided on each of the attachment ends 36 and 38 may be the same or different. The securing means 40, for example, may include a variety of mechanical, chemical, or physical means. The securing means 40 may comprise, for example, a threaded screw or bolt that passes through each end 36, 38 into a corresponding threaded fitting at locations 44, 46. The securing means 40 also may be a post that frictionally engages a cylindrical opening at locations 44, 46. Alternatively, the securing means 40 also can include a resilient flange that engages the opening 58 upon being inserted therein. In another embodiment, the securing means may include an adhesive that allows the spacer bar end 36 to be adhered to the face shield 12 at a surface 59 at location 44. Essentially any fastener suitable for joining the spacer bar 30 to the face shield 12 at opposing locations on opposing sides 18, 20 of the shield 12 may be used in connection with the present invention. One particular example is shown below in FIGS. 5a, 5b.

Figure 4:
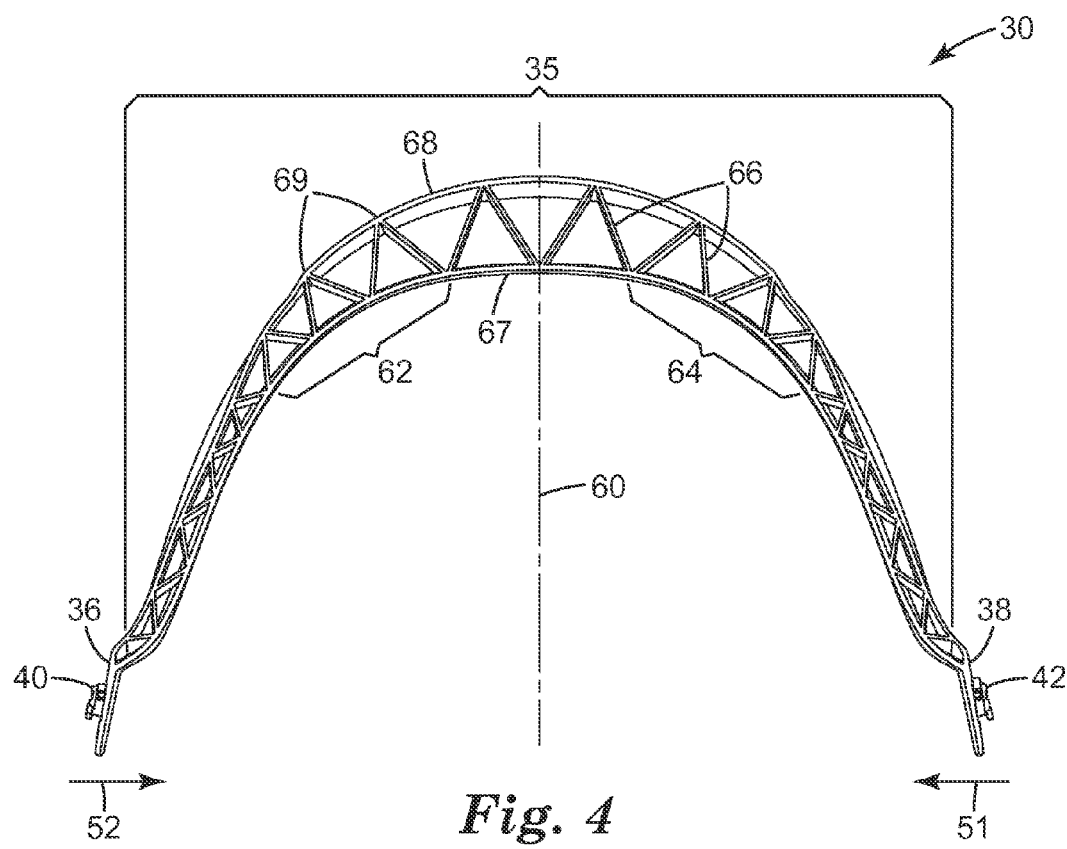
FIG. 4 shows a bottom view of a spreader bar 30 that may used in connection with the present invention.

FIG. 4 shows an example of a spreader bar 30 that may be used in accordance with the present invention. The spreader bar 30 has a bowed portion 34 located between first and second ends 36 and 38. The ends 36 and 38 may include first and second attachment means 40 and 42, respectively. The bowed portion 34 of the spreader bar 30 is essentially symmetrical about a plane 60 that bisects the spreader bar 30. The bowed portion 34 may have first and second radiused segments 62 and 64, each having a radius of curvature of about 7 to 10 cm measured from the inner sidewall 67 of the spreader bar 30. One of more trusses 66 may be provided in the spreader bar 30 to increase its stiffness or its resistance to compression in the direction of arrows 50 and 51. The trusses 66 may extend between the inner sidewall 67 and the outer sidewall 68. Each truss 66 may take the form of a triangle where the peaks 69 that meet the sidewall 67 or 68 are spaced at about 1 to 3 cm. Because the spreader bar is stiffer than the welding shield, it does not compress substantially when inserted therein. Instead, the welding shield expands as described above. The spreader bar typically has a resistance to compression of about 50 to 150 Newtons, more typically about 75 to 125 Newtons, when measured according to the Resistance to Compression Test described below. The resistance to compression of the spreader bar typically is at least about 250% greater than the resistance to compression of the welding shield when also measured according to the Resistance to Compression Test. More typically, the resistance to compression of the spreader bar is at least 500% greater than the resistance to compression of the welding shield.

Figure 5A:
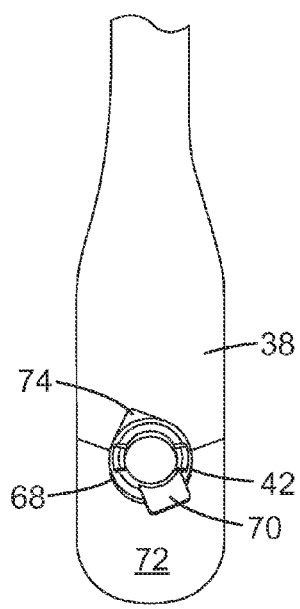
FIGS. 5a and 5b shows first and second ends 36, 38 of a spreader bar that may be used in connection with the present invention.
Figure 5B:
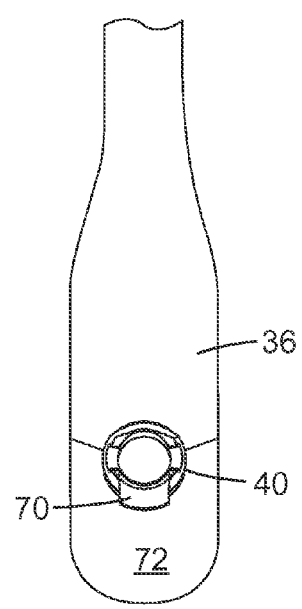

FIGS. 5a and 5b show the outer sides of the spreader bar ends 36 and 38. The first and second ends 36, 38 of the spreader bar each have a means 40, 42 for securing the respective end 36, 38 to the face shield 12. Each securing means 40, 42 includes a flange 70 that is spaced from the outer surface 72 of the end 36 or 38. When the spreader bar 30 is pushed forward within the shield 12 toward the fore area 53 and the ends 36 and 38 are pressed into the shield at locations 44 and 46, the flanges 70 can be placed through the openings 58, 58' on each side of the face shield 12 (FIG. 2). When the force pushing the spreader bar forward toward fore area 52 is released, the flange 70 engages the outer surface of face shield at the opening 58. One (or more) of the ends 38 can have an indicia or indicator 74 that points the user to the proper side of the face shield where that spreader bar end 38 engages during assembly. The indicia or indicator 74 can match a similar indicia or indicator located on the side of the face shield to which that end of the spreader bar is attached. The use of such an indicia or indicator 74 makes securement of the spreader bar to the face shield more intuitive.

EXAMPLE

Width Measurement Test

The face shield native width NW and increased width are measured at the "temporal location" on the face shield. To identify the temporal location, a transversely-extending plane bisecting the vertically oriented lens is first identified. Such a plane 80 is shown in FIG. 2. Two opposing points 82, 84 are then identified, which points are located on the bisecting plane 80 at the rearward perimeter of the face shield on each side thereof. The native width NW is where line 80 intersects the face shield perimeter at the points 82, 84 when in an unexpanded condition. The increased width is where line 80 intersects the face shield perimeter at the points 82', 84' when in an expanded condition.

Resistance to Compression Test

Face Shield Resistance to Compression:

To measure the resistance to compression of the face shield, the face shield has its opposing sides pushed together at the locations where the spreader bar is attached to the face shield. In the drawings that illustrate an embodiment of the present application, these locations would be at holes 58, 58' at locations 44, 46. The force is measured in the pushing directions 51, 52. The force is measured with the face shield in a compressed condition with the sides pressed 20 millimeters (mm) closer together. The face shield is placed in a press device and opposing sides pressed together to obtain a compression force measured using an S2 500 N load cell available from HBM, Inc. of Marlborough, Mass. The measured force represents the Face Shield Resistance to Compression.

Spreader Bar Resistance to Compression:

To measure the resistance to compression of the spreader bar, opposing ends of the spreader bar are pushed together. The spreader bar is placed in a press and force measured in a compressed condition with the opposing ends pushed 20 mm closer together. Force is measured using an S2 500 N load cell available from HBM, Inc. of Marlborough, Mass. The measured force represents the Spreader Bar Resistance to Compression.

Face Shield and Spreader Bar Assembly:

A welding shield and a spreader bar were constructed, which each had a configuration similar to the welding shield and spreader bar shown in the drawings. The spreader bar had a width W before its securement to the face shield, which width was greater than the width w of the face shield 12 between attachment locations 44, 46. The spreader bar width W and the face shield width w were both measured. The resistance to compression of the face shield and the spreader bar were measured according to the Resistance to Compression Test set forth above. The results of these tests are set forth below in Tables 1 and 2. The greater width W over w and the greater resistance to compression of spreader bar compared to face shield caused the opposing sides of the face shield to move apart when the spreader bar was installed in the face shield. The outward movement of the sides increased the distance therebetween and was great enough to allow 3M™ Peltor™ Optime™ I earmuffs to reside under each face shield side without interfering with the earmuff outer shell when the earmuffs and the inventive face shield were worn. The increase in width of the face shield from the native width NW to the increased width IW was determined according to the Width Measurement Test set forth above. The results of the spreader bar use are set forth below in Table 2:

TABLE 1

| Without Spreader Bar Insertion | |
|---|---|
| Spreader Bar Width W | 28 cm |
| Face Shield Width w | 25 cm |
| (W − w)/w × 100 | 12% |
| Face Shield Resistance to Compression (FSRTC) | 11.5 N |
| Face Shield Native Width | 25 cm |

TABLE 2

| Spreader Bar Secured to Faceshield | |
|---|---|
| Face Shield and Spreader Bar Resistance to Compression | 97 N |
| Spreader Bar Resistance to Compression | 85 N |
| Face Shield Increased Width | 28 cm |
| IW − NW | 3 cm |

This invention may take on various modifications and alterations without departing from its spirit and scope. Accordingly, this invention is not limited to the above-described but is to be controlled by the limitations set forth in the following claims and any equivalents thereof.

This invention also may be suitably practiced in the absence of any element not specifically disclosed herein.

All patents and patent applications cited above, including those in the Background section, are incorporated by reference into this document in total. To the extent there is a conflict or discrepancy between the disclosure in such incorporated document and the above specification, the above specification will control.

What is claimed is:

1. A welding shield that comprises:
   a face shield that has a native width;
   a lens disposed in the face shield; and
   a spreader bar configured to be attached to the face shield to expand the face shield from the native width to an increased width, wherein the spreader bar is stiffer than the face shield.

2. The welding shield of claim 1, wherein the spreader bar comprises first and second attachment ends.

3. The welding shield of claim 2, wherein the spreader bar comprises an arcuate portion located between the first and second attachment ends.

4. The welding shield of claim 1, wherein a width of the spreader bar between first and second attachment ends is greater than the native width of the face shield, when the spreader bar is not attached to the face shield.

5. The welding shield of claim 1, wherein the width of the spreader bar between first and second attachment ends is between 10 percent and 30 percent greater than the native width of the face shield, when the spreader bar is not attached to the face shield.

6. The welding shield of claim 1, wherein the width of the spreader bar is between 20 and 40 cm.

7. The welding shield of claim 1, wherein an expansion of the face shield from the native width to the increased width is between 2 cm and 10 cm.

8. The welding shield of claim 1, wherein the spreader bar has a resistance to compression of at least about 30 Newtons when tested according to the Resistance to Compression Test.

9. The welding shield of claim 1, wherein the spreader bar has a resistance to compression of between 50 and 150 Newtons when tested according to the Resistance to Compression Test.

10. A welding shield comprising:
    a face shield that has a native width; and
    a spreader bar configured to be attached to the face shield to expand a width of the face shield, wherein spreader bar comprises a bowed portion and first and second shield attachment ends, the bowed portion being located between the first and second attachment ends, wherein the bowed portion and the attachment ends provide the spreader bar with a resistance to compression of at least about 30 Newtons when tested according to the Resistance to Compression Test.

11. The welding shield of claim 10, wherein the spreader bar has a resistance to compression of between 50 and 150 Newtons when tested according to the Resistance to Compression Test.

12. The welding shield of claim 10, wherein the first and second attachment ends comprise flanges.

13. The welding shield of claim 10, wherein the width of the spreader bar is between 20 and 40 cm.

14. The welding shield of claim 10, wherein the bowed portion is symmetrical about a plane that bisects the spreader bar.

15. The welding shield of claim 10, wherein the spreader bar comprises indicia identifying a desired orientation.

16. The welding shield of claim 10, wherein the bowed portion comprises first and second radiused segments.

17. The welding shield of claim 16, wherein the first and second radiused segments have a radius of curvature between 7 cm and 10 cm.

18. The welding shield of claim of 1, wherein the spreader bar comprises one or more trusses extending between an inner sidewall of the spreader bar and an outer sidewall of the spreader bar.

* * * * *

UNITED STATES PATENT AND TRADEMARK OFFICE
CERTIFICATE OF CORRECTION

PATENT NO. : 9,596,902 B2
APPLICATION NO. : 14/291506
DATED : March 21, 2017
INVENTOR(S) : Daniels et al.

Page 1 of 1

It is certified that error appears in the above-identified patent and that said Letters Patent is hereby corrected as shown below:

In the Specification

Column 2
Line 35, before "used" insert -- be --.
Line 62, delete "use" and insert -- use. --, therefor.

Column 3
Line 35, delete "Tactial," and insert -- Tactical, --, therefor.

In the Claims

Column 8
Line 33, in Claim 18, after "claim" delete "of".

Signed and Sealed this
Thirtieth Day of May, 2017

Michelle K. Lee
*Director of the United States Patent and Trademark Office*